United States Patent [19]
Cameron et al.

[11] Patent Number: 5,962,750
[45] Date of Patent: *Oct. 5, 1999

[54] PROCESS THAT INVOLVES THE OPTIMUM ETHERIFICATION OF A HYDROCARBON FRACTION THAT CONTAINS OLEFINS THAT HAVE 6 CARBON ATOMS PER MOLECULE

[75] Inventors: Charles Cameron, Paris; Alain Forestiere, Vernaison; Marie-Claire Marion, Villeurbanne; Jean-Luc Nocca, Rueil Malmaison; Jean-Luc Duplan, Irigny, all of France

[73] Assignee: Institut Francais Du Petrole, France

[*] Notice: This patent issued on a continued prosecution application filed under 37 CFR 1.53(d), and is subject to the twenty year patent term provisions of 35 U.S.C. 154(a)(2).

[21] Appl. No.: 08/602,064

[22] Filed: Feb. 15, 1996

[30] Foreign Application Priority Data

Feb. 15, 1995 [FR] France ................................. 95 01813
Feb. 15, 1995 [FR] France ................................. 95 01814
Jan. 30, 1996 [FR] France ................................. 96 01052

[51] Int. Cl.⁶ .................................................. C07C 41/00
[52] U.S. Cl. .......................................... 568/697; 568/698
[58] Field of Search .............................................. 568/697

[56] References Cited

U.S. PATENT DOCUMENTS

| | | | |
|---|---|---|---|
| 3,902,870 | 9/1975 | Rohllmann et al. | 568/697 |
| 4,647,703 | 3/1987 | Torck et al. | 568/679 |
| 5,132,467 | 7/1992 | Haag et al. | 568/698 |
| 5,166,455 | 11/1992 | Chin et al. | 568/697 |
| 5,196,612 | 3/1993 | Ward | 568/697 |
| 5,198,590 | 3/1993 | Sofranko et al. | 568/698 |
| 5,264,635 | 11/1993 | Lee et al. | 568/697 |
| 5,276,212 | 1/1994 | Luebke et al. | 568/697 |
| 5,283,373 | 2/1994 | Luebke et al. | 568/697 |
| 5,420,360 | 5/1995 | Chin et al. | 568/697 |
| 5,536,887 | 7/1996 | Minkkinen et al. | 568/698 |

FOREIGN PATENT DOCUMENTS

| | | |
|---|---|---|
| 451989 | 10/1991 | European Pat. Off. . |
| 454304 | 10/1991 | European Pat. Off. . |
| 667 329 | 2/1995 | European Pat. Off. . |
| 2255090 | 4/1991 | United Kingdom . |
| 2 278 354 | 11/1994 | United Kingdom . |
| 2278354 | 11/1994 | United Kingdom . |
| 89/11463 | 11/1989 | WIPO . |

*Primary Examiner*—Dwayne C. Jones
*Attorney, Agent, or Firm*—Millen, White, Zelano & Branigan, P.C.

[57] ABSTRACT

A process for treating a feedstock containing olefins of 6 carbon atoms per molecule, said olefins being either potentially etherifiable or (directly) etherifiable, wherein isomerization of a portion of the potentially etherifiable olefins is accomplished in part in an isomerization zone, in the presence of an isomerization catalyst that makes it possible to obtain an isomerization effluent which comprises in part etherifiable olefins, and in that, in part, etherification is carried out, in the presence of an etherification catalyst and at least one alcohol that has 1 to 4 carbon atoms per molecule, of a portion of etherifiable olefins that are contained in the feedstock, in a first etherification zone, and in part etherification is carried out of a portion of etherifiable olefins that are contained in said isomerization effluent, in a second etherification zone, in the presence of an etherification catalyst and at least one alcohol that has 1 to 4 carbon atoms per molecule, to optimize the production of ethers.

15 Claims, 3 Drawing Sheets

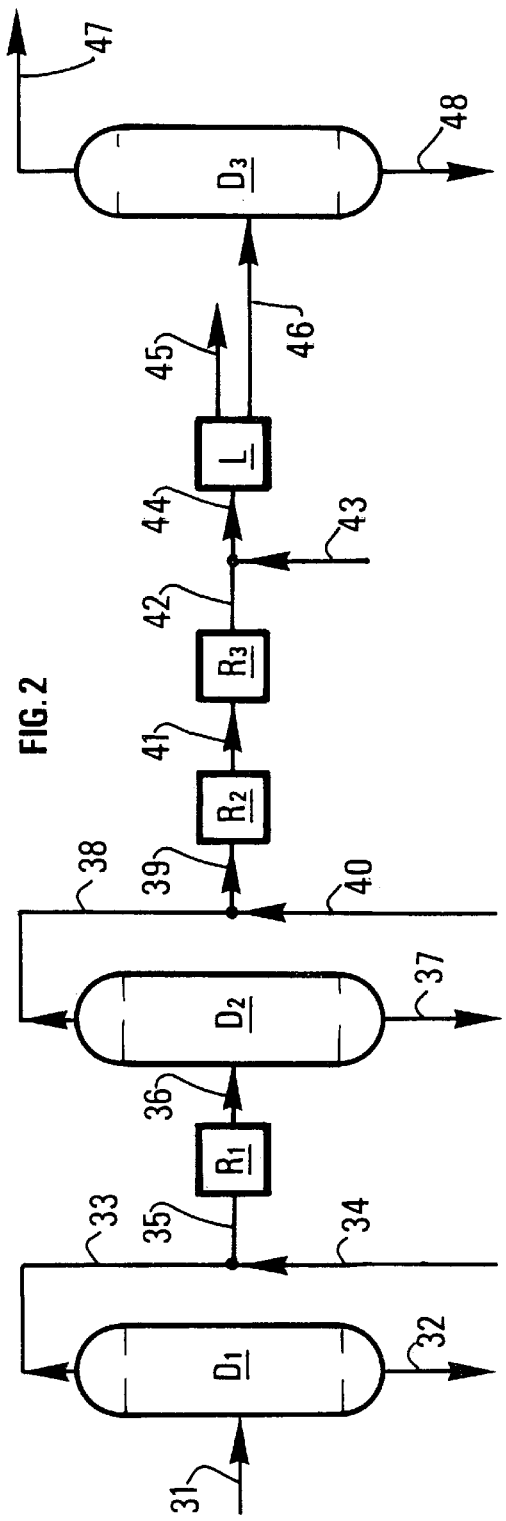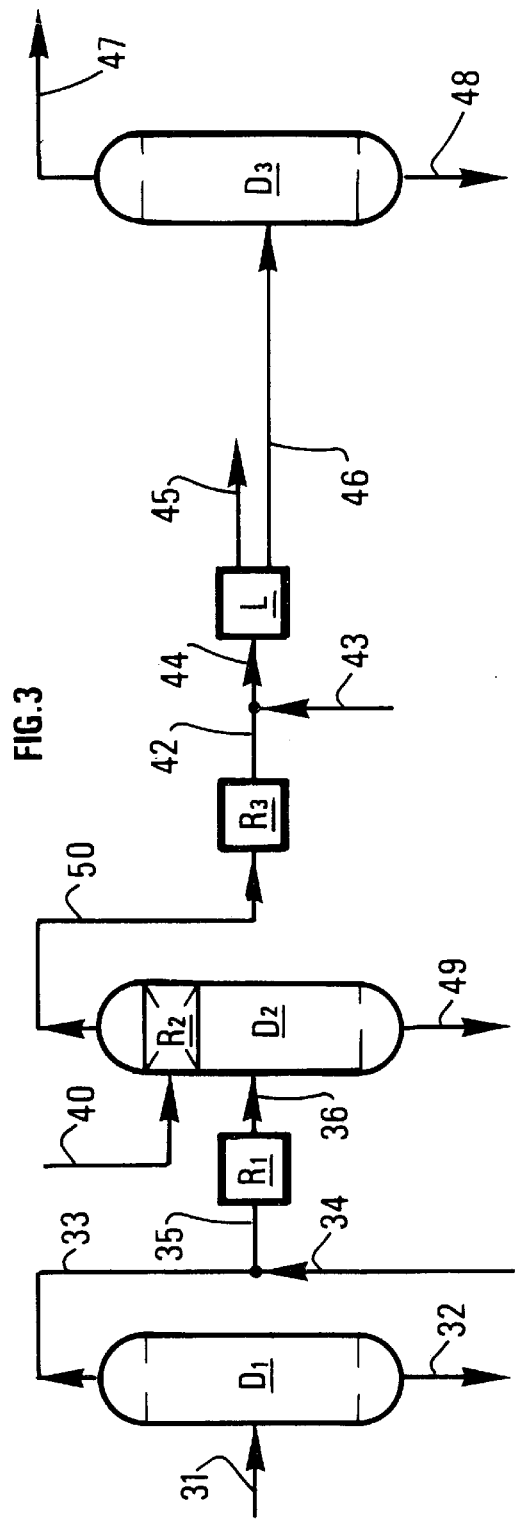

PROCESS THAT INVOLVES THE OPTIMUM ETHERIFICATION OF A HYDROCARBON FRACTION THAT CONTAINS OLEFINS THAT HAVE 6 CARBON ATOMS PER MOLECULE

SUMMARY OF THE INVENTION

This application is copending with Ser. No. 08/602,065, which is incorporated by reference in its entirety herein.

This invention relates to a process that is optimized for the etherification of olefinic fractions that are derived in particular from the dimerization or oligomerization of light olefins. It also relates to a process for obtaining fuels from a hydrocarbon mixture that contains olefinic hydrocarbons that have 6 carbon atoms per molecule. The process according to the invention comprises an etherification stage, in an etherification zone, of a portion of the etherifiable olefins of the feedstock, a stage for isomerization of a portion of the potentially etherifiable olefins of the feedstock into an isomerate that in part comprises etherifiable olefins, and an etherification stage, in a second etherification zone that is separate from the first etherification zone, of a portion of the isomerate. The invention also relates to the products that are obtained by the process. Finally, the invention also relates to a process for improving the quality of olefinic fuels and in particular those that are produced by oligomerization of light olefins.

The hydrocarbon mixtures that are used as fuels and that contain olefinic hydrocarbons are volatile compositions (since they most often contain large proportions of hydrocarbons that have fewer than 6 carbon atoms). The laws that are being enacted almost everywhere in the world are imposing new constraints on both the volatility of gasolines and on their olefin contents, which greatly limits the use of volatile olefinic compounds as fuels.

In addition, ethers, in particular those having more than 6 carbon atoms per molecule, are fuel additives whose importance, as far as their good octane number is concerned, is certain. For example, patent application PCT WO 95/16763 describes the use of 2-methoxy 2,3-dimethylbutane (MDMB) as a fuel additive, with said ether being produced by dimerization of olefin $C_3$, then by etherification in the presence of methanol. Such a production process is not optimum, however, in view of the presence in the dimerization effluent of olefins that are not directly etherifiable.

By etherification of the maximum possible olefins that are present in the feedstock, and in particular hexenes, the process according to the invention makes it possible to reduce both the steam pressure and the olefin content in the gasolines produced. Furthermore, said process makes it possible to produce gasolines that contain oxidized compounds that are desirable owing in particular to their good octane numbers (RON and MON) and, by the addition of chemically bonded alcohols, to increase the overall amount of fuel ultimately produced. The process according to the invention makes it possible to develop olefinic fractions that contain olefins that have 6 carbon atoms per molecule. One of the objects of the process according to the invention is to optimize the production of ethers from a feedstock that comprises hydrocarbons that contain in part, and preferably in large part, olefins that contain 6 carbon atoms per molecule.

The invention relates to a process for the production of ethers from a feedstock that comprises hydrocarbons that contain in part, preferably in large part, olefins that contain 6 carbon atoms per molecule, with said olefins being either potentially etherifiable or (directly) etherifiable, such that the isomerization of a portion of potentially etherifiable olefins is achieved in part in an isomerization zone, in the presence of an isomerization catalyst that makes it possible to obtain an isomerization effluent which comprises, in part, etherifiable olefins, and in that the etherification of a portion of etherifiable olefins that are contained in the feedstock is carried out in the presence of an etherification catalyst and with at least one alcohol that has 1 to 4 carbon atoms per molecule, preferably methanol, in a first etherification zone, and etherification is carried out of a portion of etherifiable olefins that are contained in said isomerization effluent, in a second etherification zone that is separate from the first etherification zone, in the presence of an etherification catalyst and with at least one alcohol that has 1–4 carbon atoms per molecule, preferably methanol.

The (directly) etherifiable olefins of the feedstock are tertiary olefins, i.e., ones that are able to provide triply substituted carbon atoms. The potentially etherifiable olefins of the feedstock are primary or secondary olefins, i.e., they are not able to provide triply substituted carbon atoms, just mono- or disubstituted carbon atoms.

According to an embodiment of the process according to the invention, the feedstock of the isomerization zone comprises virtually no ethers and preferably comprises no alcohol(s).

One of the preferred embodiments of the process a according to the invention is such that said process comprises the following successive stages:

(1) the etherification of a portion of etherifiable olefins that are contained in the feedstock, in the presence of at least one alcohol that has 1 to 4 carbon atoms per molecule and of an etherification catalyst, in a first etherification zone, (2) the separation, in a separation zone, of a large portion of the effluent of stage (1), into a first effluent that comprises, in large part, ethers that are almost pure, and a second effluent that comprises hydrocarbons, (3) the isomerization of a portion of the potentially etherifiable olefins that are included in the second effluent of stage (2) in an isomerization zone, in the presence of an isomerization catalyst that makes it possible to obtain an isomerization effluent that comprises in part etherifiable olefins, (4) etherification, in the presence of at least one alcohol that has 1 to 4 carbon atoms per molecule and an etherification catalyst, in a second etherification zone, of a portion of etherifiable olefins that are included in said isomerization effluent.

In this case, the process according to the invention is preferably such that the isomerization is hydroisomerization, or generally the transformation, in the presence of a gas flow that contains hydrogen, of a carbon-carbon double bond into another carbon-carbon double bond which, if it is internal, is such that one of the carbons is doubly substituted, i.e., said carbon-carbon double bond is triply substituted, and, if it is external, said carbon-carbon double bond is doubly substituted. Then, isomerization is carried out in the presence of a gas flow that contains hydrogen.

In the case where the isomerization stage is a hydroisomerization stage, said stage can also be carried out in a specially arranged portion of the separation zone, in the case where said zone is a distillation zone. Thus, stages (2) and (3) are carried out in a single reaction zone in the case where there is no intermediate stage between the latter. In this case, hydrogen is introduced into a zone of the distillation column where of at least one hydroisomerization catalyst bed was specially arranged, with said beds being optionally by distillation plates in the preferred case where at least two beds are present. In particular, the hydroisomerization catalysts are perfectly suited for operation in a liquid medium and therefore for so-called reactive distillation technology, i.e., a technology in which reaction and distillation are carried out simultaneously.

In the context of this invention, it is also possible to carry out hydroisomerization and etherification (stages (3) and (4)) in a single reaction zone, in the case where the latter are not separated by any intermediate stage, by using bifunctional catalysts of the type described by BP Chemical in Hydrocarbon Processing, May 1992, pages 86–88, for example, resins that are loaded on palladium.

Another preferred embodiment of the process according to the invention, according to a first variant, which is preferred over the two other variants described below, is such that said process comprises the following successive stages:

(1) the etherification of a portion of the etherifiable olefins that are contained in the feedstock, in the presence of at least one alcohol that has 1 to 4 carbon atoms per molecule and of an etherification catalyst, in a first etherification zone, (2) the separation, in a separation zone, of a portion of the effluent of stage (1), into a first effluent that comprises, in large part, ethers that are almost pure, and into a second effluent that comprises hydrocarbons, (2') washing with water of a large portion of the second effluent of stage (2) in a washing zone that makes it possible to obtain a first effluent that comprises mainly alcohol and water and a second effluent that comprises mainly hydrocarbons, (3) isomerization of a portion of the potentially etherifiable olefins that are included in the second effluent of stage (2') in an isomerization zone, in the presence of an isomerization catalyst that makes it possible to obtain an isomerization effluent that comprises in part etherifiable olefins, (4) etherification, in the presence of at least one alcohol that has 1 to 4 carbon atoms per molecule and an etherification catalyst, in a second etherification zone, of a portion of etherifiable olefins that are included in said isomerization effluent.

Another preferred embodiment of the process according to the invention, according to a second variant, is such that said process comprises the following successive stages:

(1) the etherification of a portion of etherifiable olefins that are contained in the feedstock, in the presence of at least one alcohol that has 1 to 4 carbon atoms per molecule and of an etherification catalyst, in a first etherification zone, (1') washing with water of a large portion of the effluent of stage (1) in a washing zone that makes it possible to obtain a first effluent that comprises mainly alcohol and water and a second effluent that comprises mainly hydrocarbons and ethers, (2) the separation, in a separation zone, of a large portion of the second effluent of stage (1'), into a first effluent that comprises, in large part, ethers that are almost pure, and a second effluent that comprises, in large part, hydrocarbons, (3) the isomerization of a portion of the potentially etherifiable olefins that are included in the second effluent of stage (2) in an isomerization zone, in the presence of an isomerization catalyst that makes it possible to obtain an isomerization effluent which comprises in part etherifiable olefins, (4) etherification, in a second etherification zone, in the presence of at least one alcohol that has 1 to 4 carbon atoms per molecule and an etherification catalyst, of a portion of etherifiable olefins that are included in said isomerization effluent.

Another preferred embodiment of the process according to the invention, according to a third variant, is such that said process comprises the following successive stages:

(1) etherification of a portion of the etherifiable olefins that are contained in the feedstock, in the presence of at least one alcohol that has 1 to 4 carbon atoms per molecule and an etherification catalyst, in a first etherification zone, (1') washing with water of a large portion of the effluent of stage (1) in a washing zone that makes it possible to obtain a first effluent that comprises mainly a portion of alcohol and water and a second effluent that comprises mainly hydrocarbons, ethers, and the other portion of alcohol, (2) the separation, in a separation zone, of a large portion of the second effluent of stage (1'), into a first effluent that comprises, in large part, ethers that are almost pure, and into a second effluent that comprises, in large part, the hydrocarbons and the other portion of alcohol, (2') washing with water of a large portion of the second effluent of stage (2) in a washing zone, making it possible to obtain a first effluent that comprises mainly the other portion of alcohol and water and of a second effluent that comprises mainly hydrocarbons, (3) the isomerization of a portion of the potentially etherifiable olefins included in the second effluent of stage (2') in an isomerization zone, in the presence of an isomerization catalyst that makes it possible to obtain an isomerization effluent which includes in part etherifiable olefins, (4) etherification, in a second etherification zone, in the presence of at least one alcohol that has 1 to 4 carbon atoms per molecule and of an etherification catalyst, of a portion of etherifiable olefins included in said isomerization effluent.

Regardless of the embodiment of the process according to the invention, the alcohol that is used in the etherification zone and has 1 to 4 carbon atoms per molecule is preferably methanol.

Regardless of the embodiment of the process according to the invention, the effluent of stage (4) comprises ethers, alcohol(s), and hydrocarbons.

In the case of the other preferred embodiment of the process according to the invention, regardless of the variant, the process according to the invention is preferably such that the isomerization is a skeletal isomerization, or generally the transformation of the skeleton of one portion of olefins, whereby it is possible for any olefin to be transformed into an olefin whose carbon-carbon double bond is doubly substituted if it is external and triply substituted if it is internal. However, the isomerization can also be hydroisomerization, as defined above.

Preferably, the process according to the invention, in one of the two preferred embodiments described above, generally also comprises a stage prior to stage (1), stage (0), in which the feedstock is separated into a first effluent that comprises mainly hydrocarbons which contain more than six (six excluded) carbon atoms per molecule and into a second effluent that comprises mainly hydrocarbons that contain at most six (six included) carbon atoms per molecule, with the second effluent comprising in large part the feedstock of stage (1). This stage is generally necessary, in particular if the feedstock comprises a significant part of hydrocarbons that include more than six (six excluded) carbon atoms per molecule.

Preferably, the process according to the invention, in one of the two preferred embodiments described above, is such that the separation of stage (2) is a distillation process.

According to one of the two preferred embodiments described above, in a first case, a portion, preferably a large portion, of the effluent of stage (4) can be washed in stage (5) with water in a zone for washing with water, making it possible to obtain a first effluent that comprises mainly alcohol and water and a second effluent that comprises mainly hydrocarbons.

In this case, preferably a large portion of the second effluent is, in a stage (6), distilled into a bottom effluent that comprises, in large part, ethers that are almost pure, and a top effluent that comprises, in large part, hydrocarbons.

According to one of the two preferred embodiments described above, in a second case, one portion, preferably a large portion, of the effluent of stage (4) can be distilled, in stage (5) in a distillation zone, into a bottom effluent that comprises, in large part, ethers that are almost pure and a top effluent that comprises, in large part, hydrocarbons and alcohol. It is possible to add at least one portion of the first effluent of stage (2) to the feedstock of stage (5).

In this case, preferably a large portion of the top effluent is, in a stage (6), washed with water in a zone for washing with water that makes it possible to obtain a first effluent that comprises mainly alcohol and water and a second effluent that comprises mainly hydrocarbons.

In addition, the process according to the invention optionally comprises an additional stage, stage (3'), for distillation, in an additional distillation zone, of the isomerization effluent, which makes it possible to eliminate, in the top effluent, light hydrocarbons, i.e., those that include less than six (six excluded) carbon atoms per molecule and are formed as by-products during isomerization, and to recover in the bottom effluent a purified isomerization effluent which is used in a large portion of feedstock at stage (4).

The invention also relates to any ether obtained by a process as described above, any fuel additive that comprises at least one such ether, and any fuel that comprises at least one such additive.

Since all olefins are not directly etherifiable, the process according to the invention comprises an isomerization reaction that transforms a portion of the non-etherifiable (but potentially etherifiable) olefins into etherifiable olefins, which are, in turn, by etherification, transformed in part into oxidized compounds that are desirable owing to their good octane numbers and can be incorporated into gasolines.

The feedstock of the process according to the invention can be selected from the effluents of catalytic cracking, of steam cracking, and production units for olefins, including a unit for dimerization and oligomerization of light olefins. The feedstock of the process according to the invention comprises olefinic compounds that have 6 carbon atoms per molecule, generally from 30 to 100% by weight, preferably 70 to 100% by weight and, even more preferably, 80 to 100% by weight of said compounds. The proportion of etherifiable olefins included in the feedstock, relative to the total olefins (directly or potentially etherifiable), is generally between 45 and 80%, and preferably between 50 and 70% by weight. The feedstock preferably comes from processes of dimerization or oligomerization of olefins that comprise 2 or 3 carbon atoms per molecule, described below.

Thus, the oligomerization processes of the propylene by acid catalysis or by organometallic catalysis in a homogenous phase, as in the case of the DIMERSOL G process, lead to, among other things, the production of nonlinear and therefore branched olefins.

Moreover, the process of oligomerization of the ethylene or ethylene/propylene mixtures by organometallic catalysis in a homogenous phase, known by the name DIMERSOL E, also leads to, among other things, the production of nonlinear and therefore branched olefins.

The DIMERSOL processes (registered trademark) are described by BENEDEK et al. in Oil and Gas Journal, April 1980, pp. 77–83, but it is also possible to find a general description of the DIMERSOL processes in the patents of the applicant, in particular including U.S. Pat. No. 4,283,305; U.S. Pat. No. 4,398,851; U.S. Pat. No. 4,366,087; U.S. Pat. No. 4,398,049.

The processes for oligomerization of light olefins by heterogeneous catalysis and using metals such as nickel, fixed on mineral or organic substrates, also lead, among other things, to nonlinear and therefore branched olefins. These processes are described in particular in patent EP-B-272 970 of the applicant.

Although olefins that come from the processes described above are preferably used, it should be noted that the origin of olefins to be etherified is not critical: actually, it is also possible to etherify and/or treat products that result from operations of cracking and-particularly catalytic cracking, steam cracking or even using any process for synthesis of olefins, such as, for example, the process known as the Fischer-Tropsch reaction, provided that said processes are able to produce olefins directly or indirectly.

It is well known to one skilled in the art that olefins that are branched and have an internal carbon-carbon double bond that is at least triply substituted or an external carbon-carbon double bond (at the end of a chain) that is doubly substituted react in the presence of an acid catalyst on an alcohol to produce ethers. This reaction is used in particular to produce MTBE (methyl tert-butyl ether) or ETBE (ethyl tert-butyl ether), and then methanol or ethanol is added to 2-methylpropene or to produce TAME (tert-amyl methyl ether) or ETAE (ethyl tert-amyl ether), and then methanol or ethanol is added to 2-methyl, 1-butene and to 2-methyl, 2-butene.

There are olefins that almost do not react, or at the very least do so with difficulty, on alcohols in the presence of an acid. For example, in the case of C4 fractions, butene-1 and butene-2 linear olefins barely react or react with difficulty on alcohols in the presence of an acid. In the case of C5 fractions, the pentene-1 and pentene-2 linear olefins as well as the 3-methyl 1-butene branched olefin are present, but barely react or react with difficulty on alcohols in the presence of an acid.

Similarly, in the C6 fractions that are produced by oligomerization of ethylene or propylene, there exist linear olefins and branched olefins which are not affected by the etherification reaction and which therefore are not directly etherifiable: those whose internal carbon-carbon double bond is not triply substituted, i.e., it is mono- or disubstituted, or else those whose external carbon-carbon double bond is monosubstituted. It is therefore advantageous to develop methods that, starting from a mixture of olefins, would make it possible to transform potentially etherifiable olefins into etherifiable olefins as well as possible.

In general, for a given branched olefinic structure, the isomer that is favored at low temperature is the internal olefin with its triply substituted carbon-carbon double bond or the external olefin with its doubly substituted carbon-carbon double bond. Going from a non-etherifiable olefin to a branched olefin that is etherifiable involves putting this compound into a state of thermodynamic equilibrium at low temperature, i.e., accelerating the speed of transformation of the skeleton of the chain that contains hydrocarbon.

The catalysts, generally acid solids, which are able to bring about skeletal isomerization, are either catalysts based on zeolite, such as, for example, the ZSM-22, ZSM-23, ZSM-35 zeolites, ferrierite, SAPO and structurally similar elements, or, preferably, catalysts on a substrate with an alumina or silica-alumina base that optionally comprise titanium or else titanium and boron. A system in which an aluminum oxide promotes the skeletal isomerization of linear pentenes and the isomerization of 3-methyl, 1-butene to 2-methyl butenes that are etherifiable is described in particular in Catalyst Consultant Publishing, 1994, pages 159–163.

The skeletal isomerization of olefins generally has the drawback of forming, as by-products, light hydrocarbons by cracking (C1–C5) and heavy hydrocarbons by polymerization (C7–C12).

The catalysts that are able to bring about hydroisomerization, in the presence of a gas flow that contains hydrogen, are generally catalysts based on a metal from group VIII of the periodic table, such as, for example, palladium, on a substrate that is generally based on alumina, silica or silica-alumina. A system in which palladium fixed on acid resin and in the presence of hydrogen makes it possible to promote the isomerization of 3-methyl, 1-butene into 2-methyl butenes, which under the action of the same catalyst are used to treat methanol to transform it into TAME, is described in particular in Hydrocarbon Processing, May, 1992, pages 86–88. The operation is facilitated from the thermochemical standpoint by the fact that the amounts of 3-methyl, 1-butene are relatively small and do not exceed about 5 mole %.

The process according to the invention therefore comprises two etherifiable stages (stage (1) and (4)) which are carried out at least in part in separate etherification zones, with each etherification zone comprising at least one reactor, as is known to one skilled in the art, with said reactors being consecutive when there are at least two of them, operating generally in adiabatic mode and comprising at least one acid catalyst bed that is generally of the ion-exchange resin type. Said bed can be of any suitable type, for example, stationary, expanded, etc . . . . Any catalyst that is known to one skilled in the art to achieve etherification can be envisioned within the context of this invention.

Regardless of the embodiment of the process according to the invention, it is possible to add alcohol to the feedstock of the first etherification zone, as well as to that of the second etherification zone.

Regardless of the embodiment of the process according to the invention that is described above, the etherifications of the first etherification zone and of the second etherification zone are carried out in such a way that the molar ratio of alcohol(s) to etherifiable olefins is at least equal to 1:1, and preferably between 1.2:1 and 3.5:1.

This invention finally provides a means of reducing the olefinic nature of a gasoline by transforming at least a portion of the olefins contained in this gasoline into ethers whose properties are valued by fuel blenders. The almost pure ethers obtained comprise more than 70%, preferably more than 80% and, even more preferably, more than 90% by weight of ethers, with the impurities stemming in general from hydrocarbons such as olefinic products, alcohols, or products produced by the isomerization catalyst.

One of the ways of using the process according to this invention is described below in connection with FIG. 1. The use described below relates to the use of skeletal isomerization catalysts that can operate properly only in the absence of alcohol.

A hydrocarbon fraction that has, in large part, more than five carbon atoms per molecule that contains etherifiable olefins and potentially etherifiable olefins is introduced via line 1 into a distillation zone D1 from which a bottom product (which is sent directly to the gasoline pool) is recovered via line 2 and a top product that contains, in the majority, hexenes, which is treated via line 4 with a suitable amount of alcohol to provide a mixture that is introduced via line 5 into an etherification reaction section R1, is recovered via line 3. A portion of the etherifiable olefins then provides ethers that are present with excess alcohol and unreacted hydrocarbons in line 6 at the outlet of reaction section R1.

This effluent leaving R1 is introduced into a distillation zone D2 from which almost pure ethers are recovered via line 7 and a top product that contains a mixture of hexenes and alcohol is recovered via line 8. Behind etherification zone R1 and distillation zone D2, a first washing section L1 is supplied with water via line 9, then via line 20 with the distillation top effluent of D2 (line 8). At the outlet of this washing zone, an aqueous solution of alcohol (line 10) is obtained which is used to supply column to be distilled D3, on the one hand, and the hydrocarbons which via line 11 supply reactor R2, where the isomerization that transforms a portion of the potentially etherifiable olefins into etherifiable olefins is carried out.

At the outlet of reactor R2, an isomerizate that contains etherifiable hexenes is recovered via line 12 and is treated via line 13 with the proper amount of alcohol to provide a mixture that is introduced via line 14 into an etherification reaction section R3 is recovered.

Behind etherification zone R3, a second washing section L2 is supplied with water via line 9, and then via line 21 with output effluent from R3 (line 15). At the outlet of this washing zone, on the one hand, an aqueous solution of alcohol (line 17) that is used to supply column to be distilled D3 and, on the other hand, hydrocarbons and ethers (line 16), is obtained. Column to be distilled D3 is supplied via line 18, which combines the two washing waters that contain alcohol (line 10 and 17). At the top column to be distilled D3 provides alcohol (line 19) that can be recycled upstream from t he etherification zones. At the bottom, it provides purified water, which returns to washing sections L1 and L2 via line 9.

Different ways of using the process according to this invention are described below in connection with FIGS. 2 to 4. Said uses described below relate to the use of hydroisomerization catalysts.

In FIG. 2, a hydrocarbon fraction that has, in large part, more than five carbon atoms per molecule that contains etherifiable olefins and potentially etherifiable olefins is introduced via line 31 into a distillation zone D1 from which a bottom product (which is sent directly to the gasoline pool) is recovered via line 32 and a top product that contains hexenes, which is treated via line 34 with a suitable amount of alcohol to provide a mixture that is introduced via line 35 into an etherification reaction section R1, is recovered via line 33. A portion of the etherifiable olefins then provides ethers that are present with excess alcohol and with hydrocarbons that have not reacted in line 36 at the outlet of reaction section R1.

This line 36 is used to supply a distillation zone D2, from which, at the bottom, a fraction that contains virtually pure ethers that can be used as such is recovered at the bottom via line 37 and a hydrocarbon fraction that has not reacted and excess alcohol are recovered at the top via line 38. The addition of hydrogen via line 40 makes it possible to obtain in line 39 a mixture that is used as a feedstock in a new reaction zone R2 where the hydroisomerization reaction that transforms a portion of potentially etherifiable olefins into etherifiable olefins is carried out. The discharge of the hydroisomerization reactor is done via line 41 that is used to supply a new etherification zone R3, which makes it possible to partially reconvert etherifiable olefins. In R3 (second etherification zone downstream from the first etherification zone), the conversion of etherifiable olefins can be optimized by the introduction of additional alcohol via a line, not shown.

Effluent line 42 of this etherification zone is treated with water via line 43 and supplies via line 44 the feedstock from a washing section L that makes it possible to separate via line 45 a hydrocarbon fraction in a mixture with the ethers that are formed in etherification zone R3 from an alcohol solution in water, which via line 46 supplies a distillation section D3, which allows the recovery of alcohol via line 47 (this alcohol is then recycled to line 34), is provided via line 44, and at the bottom the water which is preferably recycled, in a majority, to line 33 is provided via line 48.

The effluent that is conveyed via line 45 can be distilled, if necessary, in a column that is similar to distillation D2, and in this case which is not depicted in the diagram of FIG. 2 at the top, a fraction that contains hydrocarbon is then obtained at the top, and almost pure ethers, which can be mixed with those obtained via line 37, are obtained at the bottom.

FIG. 3 is a variant of FIG. 2, in which hydroisomerization section R2 is integrated with distillation column D2.

After a distillation zone D1 and an etherification zone R1 that are similar to those already seen in FIG. 2, a separation section D2, which makes it possible to obtain, as in the preceding case, via line 49 a fraction of almost pure ethers, is supplied via line 36; but section D2 exhibits the particular feature of being supplied in its upper portion with hydrogen (line 40). This hydrogen arrives in a zone of the column where a distillation filler that contains the same catalyst as that which made it possible to carry out the hydroisomerization reaction described in FIG. 2 was placed. Finally, FIG. 3 has combined, for the same purpose, separation function D2 and hydroisomerization function R2 of the preceding figure. A hydrocarbon mixture that contains etherifiable olefins, non-etherifiable olefins, some paraffins, and excess alcohol is thus conveyed via line 50.

The discharge of the hydroisomerization reactor is done via line 50, which is used to supply a new etherification zone R3, which makes it possible to partially reconvert the etherifiable olefins. An input of alcohol via a line that is not shown makes it possible to optimize the conversion of olefins in etherification zone R3.

The effluent, line 42, from this etherification zone, is treated with water via line 43 and provides, via line 44, the feedstock for a washing section L that makes it possible to separate via line 45 a hydrocarbon fraction in a mixture with the ethers that are formed in etherification zone R3 of an alcohol column in water that, via line 46, supplies a distillation section D3 which allows the recovery of alcohol via line 47 (this alcohol is then recycled to line 34) and, at the bottom, via line 48, water that is preferably recycled, in the majority, to line 43.

The effluent that is conveyed via line 45 can be distilled, if necessary, in a column that is similar to distillation D2, and in this case, which is not shown in the diagram of FIG. 3, a fraction that contains hydrocarbon is then obtained at the top, and almost pure ethers that can be mixed with those obtained via line 49 are obtained at the bottom.

FIG. 4 makes it possible to develop a more compact system than that indicated in FIG. 2.

After a distillation zone D1 and an etherification zone R1 that are similar to those already seen in FIG. 2, a separation section D2 is supplied that makes it possible to obtain, as in the preceding case of FIG. 2, a fraction of almost pure ethers via line 37 and a mixture of hydrocarbons and alcohol that is used in excess via line 38. After hydrogen has been introduced via line 40, this mixture is used as a feedstock (line 39) in a single reactor (R2+R3), where the operation of hydroisomerization and that of etherification are carried out, for example, successively or concomitantly. To do this, the reactor contains at least a first hydroisomerization catalyst bed, then at least one ion-exchange resin bed of the acid type that makes possible the etherification reaction. This arrangement is made possible because the conditions of the two reactions are very similar both in terms of pressure level and temperature. It is also possible to use a mixture of the two catalysts or even a bifunctional single catalyst of the type of the one described in Hydrocarbon Processing, May 1992, pages 86–88, for example, a catalyst with palladium deposited on an ion-exchange resin of the acid type. An addition of alcohol can also be introduced via a line, not shown, to optimize the conversion of olefins in mixed zone R2+R3.

The effluent from this reactor R2+R3 then supplies a washing system L and then a column D3, devices whose operation has already been described in FIG. 2.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding French application 95/01813, filed Feb. 15, 1995, are hereby incorporated by reference.

BRIEF DESCRIPTION OF THE DRAWINGS

FIG. 2 is a schematic diagram of a second embodiment of the invention. A hydrocarbon fraction is introduced via line 31 into a distillation zone (D1). A hexene fraction is recovered via line 33 and treated with alcohol via line 34 to provide a mixture that is introduced, via line 35, into an etherification reaction zone (R1). The effluent from R1 is introduced into a distillation zone (D2) from which almost pure ethers are recovered via line 37 and a fraction containing unreacted hydrocarbons and alcohol is recovered via line 38. The unreacted hydrocarbon and alcohol fraction is mixed with hydrogen via line 40 and the mixture is introduced via line 39 to hydroisomerization reaction zone (R2). The effluent of R2 is supplied to an etherification reaction zone (R3). The effluent from R3 is treated with water via line 43 and the mixture is introduced into the washing zone (L) via line 44. A hydrocarbon fraction is recovered from L via line 45 and an alcohol and water fraction is recover from L via line 46. The alcohol and water fraction is then distilled in distillation zone (D3) to recover alcohol via line 47 and water via line 48.

FIG. 3 is a variant of FIG. 2 and is a schematic diagram of a third embodiment of the invention. After a distillation zone (D1) and an etherification reaction zone (R1), as described for FIG. 2, the R1 effluent is introduced via line 36 to a separation zone (D2). D2 is also supplied with hydrogen via line 40 which arrives in a zone of D2, indicated as R2, having a distillation filler that contains a hydroisomerization catalyst. A hydrocarbon mixture is conveyed via line 50 to etherification reaction zone (R3), and the remainder of the system is as described above for FIG. 2.

EXAMPLES

Figure 1:
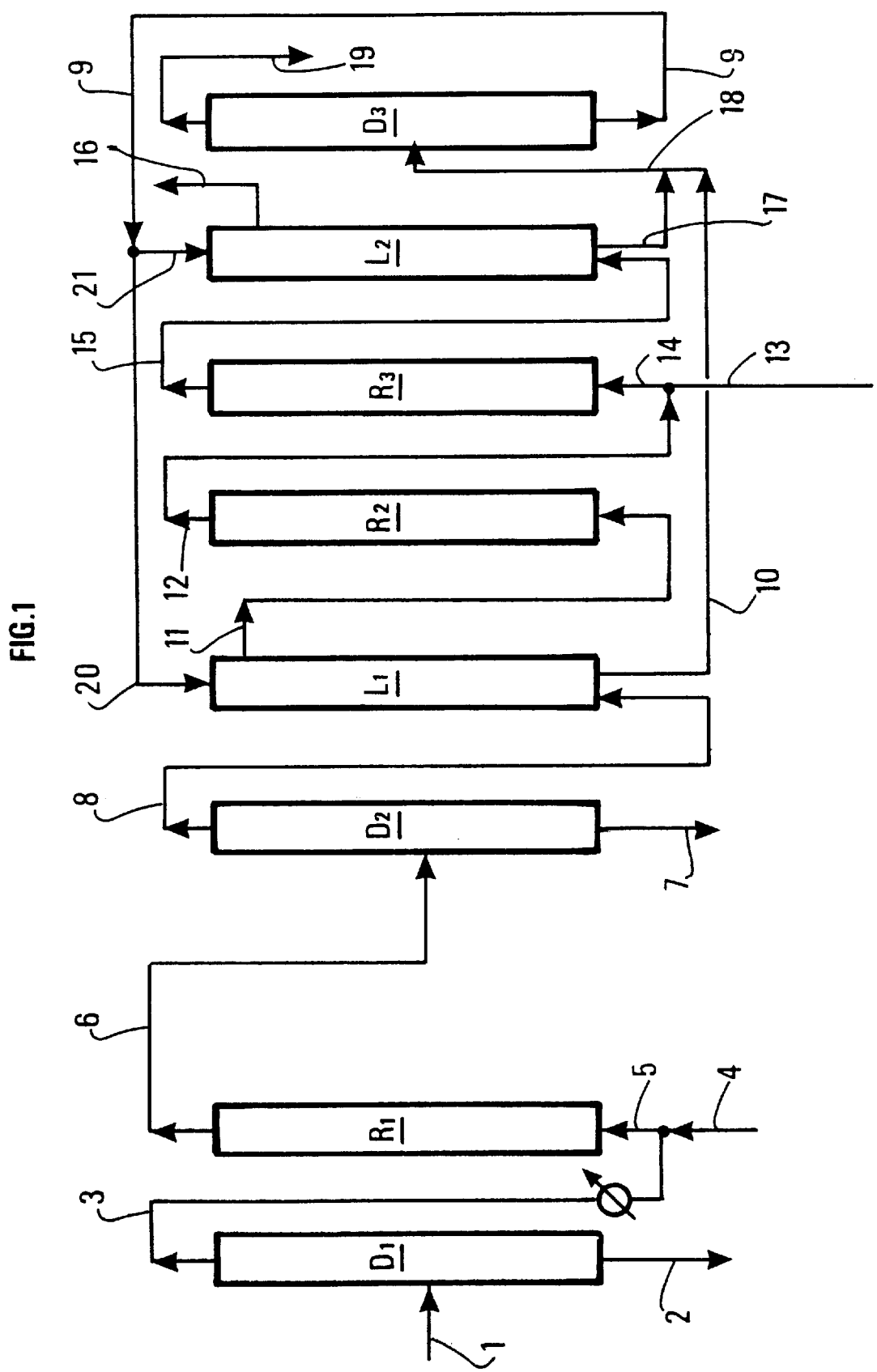
FIG. 1 is a schematic diagram of one embodiment of the invention. A hydrocarbon fraction is introduced via line 1 into a distillation zone (D1). A hexene fraction is recovered via line 3 and treated with alcohol via line 4 to provide a mixture that is introduced, via line 5, into an etherification reaction zone (R1). The effluent from R1 is introduced into a distillation zone (D2) from which almost pure ethers are recovered via line 7 and a fraction containing hexenes and alcohol is recovered via line 8. The hexene fraction is washed in washing zone (L1) which is supplied with water via lines 9 and 20. At the outlet of The washing zone, a aqueous solution of alcohol is supplied to a distillation zone (D3) via line 10 and hydrocarbons are supplied to an isomerization reaction zone (R2) via line 11. At the outlet of R2, an isomerizate that contains etherifiable hexenes is recovered via line 12 and treated via line 13 with alcohol to provide mixture that is introduced via line 14 into an etherification reaction zone (R3). A second washing zone (L2) is supplied with output effluent from R3 via line 15 and with water via lines 9 and 21. At the outlet of L2, an aqueous solution of alcohol (line 17) and a miniure of hydrocarbons and ethers (line 16) are obtained. Distillation zone (D3) is supplied via line 18, which combines two aqueous alcohol solutions (lines 10 and 17) and a water fraction and an alcohol fraction are obtained via lines 19 and 9, respectively
Figure 4:
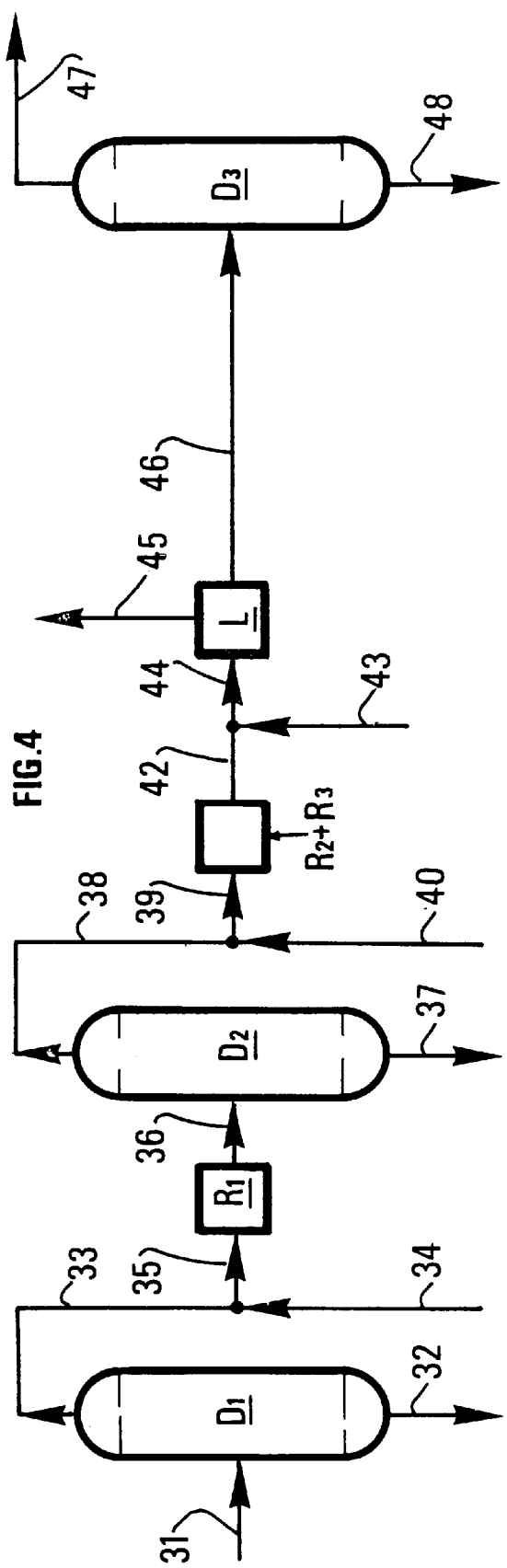
FIG. 4 is a schematic diagram of a fourth embodiment of the invention. The diagram shows a distillation zone (D1) and an etherification reaction zone (R1) as in FIG. 2. The effluent from R1 is separated in separation zone (D2) into a fraction of almost pure ethers (line 37) and a fraction containing hydrocarbons and alcohol. Hydrogen is introduced into the hydrocarbon and alcohol fraction via line 40 and the mixture is used as a feedstock via line 39 for a single reactor (R2+R3), where both hydroisomerization and etherification are carried out. The effluent from the R2+R3 reactor then supplies a washing system L via line 44, and the remainder of the system is as described above for FIG. 2.

Example 1
Case Where the Isomerization is a Skeletal Isomerization
The proposed diagram is illustrated by FIG. 1.

A hexene fraction that is obtained from a DIMERSOL G unit is introduced via line (1) into dehexanizer (column) D1, from which heavy products C7–C12 are eliminated via line (2) and a distillate which is mixed with methanol which comes in through line (4) is supplied via line (3) to form the feedstock which enters through line (5) into first etherification reactor R1. Etherification is carried out in tubular reactor R1, which is equipped with a double jacket in which a coolant circulates; the latter, maintained at 60° C., ensures temperature regulation. The pressure in the reactor is 10 bar. The catalyst that is used is a commercial sulfonic resin, supplied by Rohm and Haas (Amberlyst 15). The mixed feedstock (hydrocarbons and methanol) feeds the reactor, circulating from bottom to top (up-flow [in English]). Its flow is such that the hourly volumetric flow rate (VVH) is 0.8 $h^{-1}$. The effluent from R1, via line (6), is used as a feedstock in azeotropic distillation column D2, which eliminates almost pure ethers (7) at the bottom and which makes it possible to eliminate methanol with the hydrocarbons by azeotropy in the distillate (line (8)). The distillate from D2 (8) must be freed of methanol, which would very quickly deactivate the isomerization catalyst. Washing is carried out in washing section L1, by water via lines (9) then (20). The water-methanol mixture is then sent, via lines (10) and then (18), to column D3. Hydrocarbons (11) are sent to isomerization reactor R2. The potentially etherifiable olefins included in feedstock (1) and in line (11) are isomerized in reactor R2. The catalyst and the operating conditions are as follows:

Catalyst: based on alumina (IS-463 of the Procatalyse [Procatalysis] company)

Temperature: 380° C.

Pressure: 3 bar

VVH: 2h−1

Isomerate (12) that is obtained from R2 is mixed with methanol (13) to provide feedstock (14) for second etherification reactor R3 (under operating conditions that are identical to those of R1). Effluent (15) from R3 should be free of methanol.

Washing is carried out in washing section L2, by water via lines (9) and then (21). The water-methanol mixture is then sent via lines (17) and then (18) into column D3, with the methanol exiting via line (19) and the water being recycled into the process via line (9). Line (16) provides hydrocarbons and ethers.

On the basis of experimental results that are obtained by isomerization and by etherification (cf. Table No. 1), the flows and compositions of each flow have been calculated and are given in Table 2 (presented in three parts: Table 2A, Table 2B and Table 2C).

TABLE No. 1

| Conditions for calculating the material balance (etherification, isomerization) | |
|---|---|
| MeOH/iC6 = (eth) (mol/mol) | 1.5 |
| Conversion | |
| 3MeC5 =+EtC4 = | 51.00% |
| 2MeC5 = | 75.00% |
| 2,3DiMeC4 = | 51.00% |
| Isomerization Conditions Composition of the Output | % by Weight |
| C1–C3 | 0.77% |
| C4–C5 | 5.08% |
| 3MeC5=+EtC4= | 21.62% |
| 2MeC5= | 27.49% |
| 2,3DiMeC4= | 14.02% |
| C6 = non-etherifiable | 26.93% |
| C6 | 0.92% |
| C7–C12 | 3.17% |
| Total | 100% |

TABLE No. 2.A

| | Rates of flow in kg · h − 1 | | | | |
|---|---|---|---|---|---|
| | 1 | 2 | 3 | 4 | 5 |
| C1–C3 | | | | | |
| C4–C5 | | | | | |
| 3MeC5 =+EtC4 = | | | | | |
| 2MeC5 = | | 47 | | 47 | 47 |
| 2,3DiMeC4 = | | 8 | | 8 | 8 |
| C6 = non etherifiable C6 paraffins | | 40 | | 40 | 40 |

TABLE No. 2.A-continued

| Rates of flow in kg · h − 1 | | | | | |
|---|---|---|---|---|---|
| | 1 | 2 | 3 | 4 | 5 |
| C7–C12 | 5 | 5 | | | |
| Methanol | | | | 31.43 | 31.43 |
| TOTAL | 100 | 5 | 95 | 31.43 | 126.43 |

TABLE No. 2.B

| Rate of flow in kg · h − 1 | | | | | |
|---|---|---|---|---|---|
| | 6 | 7 | 8 | 11 | 12 |
| C1–C3 | | | | | 0.43 |
| C4–C5 | | | | | 2.83 |
| 3MeC5 =+EtC4 = | | | | | 12.04 |
| 2MeC5 = | 11.75 | | 11.75 | 11.75 | 15.3 |
| 2,3DiMeC4 = | 3.92 | | 3.92 | 3.92 | 7.81 |
| C6 = non-etherifiable | 40 | | 40 | 40 | 14.99 |
| C6 paraffins | | | | | 0.51 |
| C7–C12 | | | | | 1.77 |
| MeOH | 6.45 | | 16.45 | | |
| Water | | | | | |
| 2Et 2methoxy C4 | | | | | |
| 2Me 2methoxy C5 | 48.68 | 48.68 | | | |
| 2,3DiMe 2methoxy C4 | 5.63 | 5.63 | | | |
| TOTAL | 126.43 | 54.31 | 72.12 | 55.7 | 55.7 |

TABLE No .2.C

| Rate of Flow in kg · h− i | | | | | |
|---|---|---|---|---|---|
| | 13 | 14 | 15 | 16 | 19 |
| C1–C3 | | 0.43 | 0.43 | 0.43 | |
| C4–C5 | | 2.83 | 2.83 | 2.83 | |
| 3MeC5 = + EtC4 = | | 12.04 | 5.9 | 5.9 | |
| 2MeC5 = | | 15.3 | 3.83 | 3.83 | |
| 2,3DiMeC4 = | | 7.81 | 3.83 | 3.83 | |
| C6 = non-etherifiable | | 14.99 | 14.99 | 14.99 | |
| C6 paraffins | | 0.51 | 0.51 | 0.51 | |
| C7–C12 | | 1.77 | 1.77 | 1.77 | |
| MeOH | 20.08 | 20.08 | 11.86 | | 28.3 |
| Water | | | | | |
| 2Et 2methoxy C4 | | | 8.48 | 8.48 | |
| 2Me 2methoxy C5 | | | 15.85 | 15.85 | |
| 2,3DiMe 2methoxy C4 | | | 5.5 | 5.5 | |
| TOTAL | 20.08 | 75.8 | 75.8 | 63.9 | 28.3 |

Legend of the abbreviations used:
iC6 =: isohexenes
MeOH: methanol
3MeC5 =: 3-methylpentene
EtC4 =: ethylbutenes
2MeC5 =: 2-methyipentene
2,3DiMeC4 =: 2,3-dimethylbutene
C6 = non-etherifiable: non-etherifiable hexenes, i.e., potentially etherifiable but not directly etherifiabie, which are: hexene-1, hexene-2 (cis or trans), hexene-3 (cis or trans), methyl-3 pentene-1, methyl-4 pentene-1, methyl-4 pentene-2 (cis or trans), dimethyl-3,3 butene-1 (The etherifiable C6 olefins are as follows: methyl-2 pentene-1, methyl-2 pentene-2, methyl-3-pentene-2 (cis or trans), ethyl-2 butene-1, dimethyl-2,3 butene-1 and dimethyl-2,3 butene-2.)
2Et 2methoxy C4: 2-ethyl 2-methoxy butane
2Me 2methoxy C5: 2-methyl 2-methoxy pentane
2,3DiMe 2methoxy C4: 2,3-dimethyl 2-methoxy butane
HC: hydrocarbons Example 2
Case Where the Isomerization is a Hydroisomerization Just as in Example 1, the proposed diagram is illustrated by FIG. 1. The difference between this and Example 1 lies in the nature of the isomerization that is carried out: in Example 1 it is skeletal isomerization, while in this Example 2 it is hydroisomerization. In the case illustrated by this example, a washing step is carried out so that the feedstock for hydroisomerization is virtually free of alcohol.

The hydrocarbon feedstock is a gasoline fraction that is produced by a Dimersol commercial unit. It is distilled to eliminate the bulk of its heavy fraction (olefins of C9 and C12). At the end of the distillation operation, the C6 fraction contains no more than 5% by weight of C9 olefins. Its composition is given in Table 3.

This fraction (100 kg) is treated with methanol (39 kg) so that the ratio between methanol and directly etherifiable olefins (2-methylpentenes and 2,3-dimethylbutenes) is equal to 1.86.

The etherification is carried out in a tubular reactor R1 that is equipped with a double jacket in which a coolant circulates; the latter, maintained at 60° C., ensures temperature regulation. The pressure in the reactor is 10 bar. The catalyst that is used is a commercial sulfonic resin, provided by Rohm and Haas (Amberlyst 15). The mixed feedstock (hydrocarbon and methanol) feeds the reactor, circulating from bottom to top (up-flow). Its flow is such that the hourly volumetric flow rate (VVH) is 0.8 h−1. This first etherification stage converts the 2-methylpentenes at a level of 72.3% and the 2,3-dimethylbutenes at a level of 49%. Two ethers are formed during this stage (Table 3).

The effluent from this first etherification section is then distilled (the fraction point is set at 75° C.) to extract from it the heavy fraction, which is composed primarily of the previously formed ethers. This heavy fraction is intended for the gasoline pool (Table 4A). The effluent is washed with water to extract the residual methanol from it.

The effluent, which is free of methanol, is treated with hydrogen to produce an H2/olefin ratio of 0.1. The mixture is then introduced into a reactor that contains a palladium catalyst on an alumina substrate. The equipment is similar to that described above (etherification section). The temperature is regulated by circulation of a coolant that is maintained at 90° C. The pressure in the reactor is 10 bar. The hourly volumetric flow rate (VVH) is 5 h−1. During this operation, 74% of the 4-methylpentenes is transformed into 2-methylpentenes. A small amount of alkane is also formed, but it does not appear in the results given in Table 4B.

The effluent from this hydroisomerization section is sent back, after the addition of methanol (24.6 kg), to the etherification installation (under the identical operating conditions, except that the methanol/etherifiable olefins stoichiometry is slightly higher). In this stage, the 2-methylpentenes are converted at a level of 73.7% and the 2,3-dimethylbutenes are converted at a level of 51% (Table 4C). In a final stage, the effluent is washed to extract the residual methanol. The washed product can be sent to the gasoline pool.

The results of all the operations are given in Table 4D:

From 100 kg of C6 fraction, 82.7 kg of ethers, of which 63% is available in a nearly pure state, is obtained; it can be used directly as a fuel additive.

As a whole, this process increases the production intended for the gasoline pool by 22.8%. Furthermore, it significantly reduces the olefinic nature of the initial fraction by transforming 81.8% of methylpentenes and 75.3% of dimethylbutenes into ethers.

TABLE 3

|  | Olefinic HC feedstock (1) (kg) | HC feedstock + alcohol introduced in R1 (5) (kg) | Effluent after etherification in R1 (6) (kg) |
|---|---|---|---|
| 2-methylpentenes | 46.9 | 46.9 | 13 |
| 2,3-dimethylbutenes | 8.1 | 8.1 | 4.1 |
| 4-methylpentenes | 18.9 | 18.9 | 18.9 |
| n-hexenes | 21.1 | 21.1 | 21.1 |
| olefins of C9 | 5 | 5 | 5 |
| methanol |  | 39 | 24.6 |
| 2-methyl,2-methoxy-pentane |  |  | 46.8 |
| 2,3-dimethyl,2-methoxybutane |  |  | 5.5 |
| Total (kg) | 100 | 139 | 139 |

TABLE 4A

|  | Distillation bottom (7) | Washing top (11) |
|---|---|---|
| 2-methylpentenes |  | 13 |
| 2,3-dimethylbutenes |  | 4.1 |
| 4-methylpentenes |  | 18.9 |
| n-hexenes |  | 21.1 |
| olefins of C9 | 5 |  |
| methanol |  |  |
| 2-methyl,2-methoxypentane | 46.8 |  |
| 2,3-dimethyl,2-methoxybutane | 5.5 |  |
| TOTAL (kg) | 57.3 | 57.1 |

TABLE 4B

|  | Hydroisomerization feedstock (11) | Effluent after hydroisomerization (12) |
|---|---|---|
| 2-methylpentenes | 13 | 27 |
| 2,3-dimethylbutenes | 4.1 | 4.1 |
| 4-methylpentenes | 18.9 | 4.9 |
| n-hexenes | 21.1 | 21.1 |
| olefines of C9 |  |  |
| methanol |  |  |
| 2-methyl,2-methoxypentane |  |  |
| 2,3-dimethyl,2-methoxybutane |  |  |
| TOTAL (kg) | 57.1 | 57.1 |

TABLE 4C

|  | Feedstock of the second etherification zone (R3) (14) | Effluent after etherification (15) | Effluent after washing (L2) (16) |
|---|---|---|---|
| 2-methylpentenes | 27 | 7.1 | 7.1 |
| 2,3-dimethylbutenes | 4.1 | 2 | 2 |
| 4-methylpentenes | 4.9 | 4.9 | 4.9 |
| n-hexenes | 21.1 | 21.1 | 21.1 |
| olefins of C9 |  |  |  |
| methanol | 24.6 | 16.2 |  |
| 2-methyl,2-methoxypentane |  | 27.5 | 27.5 |
| 2,3-dimethyl,2-methoxybutane |  | 2.9 | 2.9 |
| TOTAL (kg) | 81.7 | 81.7 | 65.5 |

TABLE 4D

|  | Initial HC feedstock (1) | Pure ether output (D2 output) (7) | Effluent after washing (L2) (16) | Total production |
|---|---|---|---|---|
| 2-methylpentenes | 46.9 |  | 7.1 | 7.1 |
| 2,3-dimethylbutenes | 8.1 |  | 2 | 2 |
| 4-methylpentenes | 18.9 |  | 4.9 | 4.9 |
| n-hexenes | 21.1 |  | 21.1 | 21.1 |
| olefins of C9 | 5 | 5 |  | 5 |
| 2-methyl,2-methoxy-pentane |  | 46.8 | 27.5 | 74.3 |
| 2,3-dimethyl,2-methoxybutane |  | 5.5 | 2.9 | 8.4 |
| TOTAL (kg) | 100 | 57.3 | 65.5 | 122.8 |

Example 3
Case Where the Isomerization is Hydroisomerization

The example described below illustrates the successive operations of distillation, etherification, and isomerization, as indicated in FIG. 2. In the case illustrated by this example, no washing of the feedstock of the hydroisomerization is performed, which causes the hydroisomerization to be carried out in the presence of alcohol.

The hydrocarbon feedstock is a gasoline fraction that is produced by a Dimersol commercial unit. It is distilled to eliminate the bulk of its heavy fraction (olefins of C9 and C12). At the end of the distillation operation, the C6 fraction contains no more than 5% by weight of C9 olefins. Its composition is given in Table 5.

This fraction (100 kg) is treated with methanol (39 kg) so that the ratio between methanol and directly etherifiable olefins (2-methylpentenes and 2,3-dimethylbutenes) is equal to 1.86.

Etherification is carried out in a tubular reactor (R1) that is equipped with a double jacket in-which a coolant circulates; the latter, maintained at 60° C., ensures temperature regulation. The pressure in the reactor is 10 bar. The catalyst that is used is a commercial sulfonic resin, supplied by Rohm and Haas (Amberlyst 15). The mixed feedstock (hydrocarbon and methanol) feeds the reactor, circulating from bottom to top (up-flow). Its flow is such that the hourly volumetric flow rate (VVH) is 0.8 h−1. This first etherification stage converts the 2-methylpentenes at a level of 72.3% and the 2,3-dimethylbutenes at a level of 49%. Two ethers are formed during this stage (Table 5).

The effluent from this first etherification section is then distilled (the fraction point is set at 75° C.) to extract from it the heavy fraction, which is composed primarily of previously formed ethers. This heavy fraction is intended for the gasoline pool (Table 6A).

The light fraction (residual C6 and methanol) is treated with hydrogen to provide an H2/olefin ratio of 0.1. The mixture is then introduced into a hydroisomerization reactor (R2) that contains a palladium catalyst that is on an alumina substrate and is treated with an organic sulfur agent. The equipment is similar to that described above (etherification section). The temperature is regulated by circulation of a coolant that is maintained at 90° C. The pressure in the reactor is 10 bar. The hourly volumetric flow rate (VVH) is 5 h−1. During this operation, 74% of the 4-methylpentenes is transformed into 2-methylpentenes. A small amount of alkane is also formed, but it does not appear in the results given in Table 6B.

The effluent from this hydroisomerization section is put back into the etherification installation (under the identical operating conditions). In this stage, the 2-methylpentenes are converted at a level of 73.7% and the 2,3-dimethylbutenes are converted at a level of 51% (Table 6B). In a final stage, the effluent is washed to extract the residual methanol. The washed product can be sent to the gasoline pool.

The results of all the operations are given in Table 6C:

From 100 kg of C6 fraction, 82.7 kg of ethers, of which 63% is available in a nearly pure state, is obtained; it can be used directly as a fuel additive.

Overall, this process increases the production intended for the gasoline pool by 22.8%. Furthermore, it significantly reduces the olefinic nature of the initial fraction by transforming into ethers 81.8% of methylpentenes and 75.3% of dimethylbutenes.

TABLE 5

|  | HC feedstock (31) (kg) | HC feedstock + alcohol introduced in R1 (35) (kg) | Effluent after etherification in R1 (36) (kg) |
|---|---|---|---|
| 2-methylpentenes | 46.9 | 46.9 | 13 |
| 2,3-dimethylbutenes | 8.1 | 8.1 | 4.1 |
| 4-methylpentenes | 18.9 | 18.9 | 18.9 |
| n-hexenes | 21.1 | 21.1 | 21.1 |
| olefins of C9 | 5 | 5 | 5 |
| methanol |  | 39 | 24.6 |
| 2-methyl,2-methoxy-pentane |  |  | 46.8 |
| 2,3-dimethyl,2-methoxybutane |  |  | 5.5 |
| Total (kg) | 100 | 139 | 139 |

TABLE 6A

|  | Feedstock of the column to be distilled D2 (36) | Distillation top (38) | Distillation Bottom (37) |
|---|---|---|---|
| 2-methylpentenes | 13 | 13 |  |
| 2,3-dimethylbutenes | 4.1 | 4.1 |  |
| 4-methylpentenes | 18.9 | 18.9 |  |
| n-hexenes | 21.1 | 21.1 |  |
| olefins of C9 | 5 |  | 5 |
| methanol | 24.6 | 24.6 |  |
| 2-methyl,2-methoxy-pentane | 46.8 |  | 46.8 |
| 2,3-dimethyl,2-methoxybutane | 5.5 |  | 5.5 |
| TOTAL (kg) | 139 | 81.7 | 57.3 |

TABLE 6B

|  | Distillation front (38) | Effluent after hydroisomerization (41) | Effluent after etherification (R3) (42) | Effluent after washing (L) (45) |
|---|---|---|---|---|
| 2-methylpentenes | 13 | 27 | 7.1 | 7.1 |
| 2,3-dimethylbutenes | 4.1 | 4.1 | 2 | 2 |
| 4-methylpentenes | 18.9 | 4.9 | 4.9 | 4.9 |
| n-hexenes | 21.1 | 21.1 | 21.1 | 21.1 |
| olefins of C9 |  |  |  |  |

TABLE 6B-continued

|  | Distillation front (38) | Effluent after hydroisomerization (41) | Effluent after etherification (R3) (42) | Effluent after washing (L) (45) |
|---|---|---|---|---|
| methanol | 24.6 | 24.6 | 16.2 |  |
| 2-methyl,2-methoxy-pentane |  |  | 27.5 | 27.5 |
| 2,3-dimethyl,2-methoxybutane |  |  | 2.9 | 2.9 |
| TOTAL (kg) | 81.7 | 81.7 | 81.7 | 65.5 |

TABLE 6C

Total production of ethers relative to the initial feedstock (ethers produced in Rl and ethers produced in R3 after washing).

|  | Initial HC feedstock (31) | Output of pure ethers (D2 output) (37) | Effluent after washing (L) (16) | Total production |
|---|---|---|---|---|
| 2-methylpentenes | 46.9 |  | 7.1 | 7.1 |
| 2,3-dimethylbutenes | 8.1 |  | 2 | 2 |
| 4-methylpentenes | 18.9 |  | 4.9 | 4.9 |
| n-hexenes | 21.1 |  | 21.1 | 21.1 |
| olefins of C9 | 5 | 5 |  | 5 |
| 2-methyl,2-methoxy-pentane |  | 46.8 | 27.5 | 74.3 |
| 2,3-dimethyl,2-methoxybutane |  | 5.5 | 2.9 | 8.4 |
| TOTAL (kg) | 100 | 57.3 | 65.5 | 122.8 |

We claim:

1. A process for the production of ethers from a hydrocarbon feedstock comprising 70 to 100% by weight olefins that contain 6 carbon atoms per molecule, with said olefins containing 30 to 50% of those which are potentially etherifiable and 50 to 70% of those which are directly etherifiable, comprising successively:

(0) separating the feedstock into a $>C_6$ hydrocarbon fraction and into a $\leq C_6$ hydrocarbon fraction, (1) etherifying a portion of the etherifiable olefins that are contained in the $\leq C_6$ hydrocarbon fraction, in the presence of at least one alcohol that has 1 to 4 carbon atoms per molecule and of an etherification catalyst, in a first etherification zone to obtain an etherified effluent, (1') washing with water a portion of the etherified effluent of (1) in a washing zone that makes it possible to obtain a water and alcohol effluent and a hydrocarbon effluent, (2) separating, in a separation zone, a portion of the hydrocarbon effluent of (1'), into an ether effluent and into a hyrocarbon and alcohol effluent, (2') washing with water a portion of the hydrocarbon and alcohol effluent of (2) in a washing zone that makes it possible to obtain a water and alcohol effluent and a hydrocarbon effluent, (3) isomerizing a portion of potentially etherifiable olefins that are included in the hydrocarbon effluent of (2') in an isomerization zone, in the presence of an isomerization catalyst that makes it possible to obtain an isomerization effluent that comprises in part etherifiable olefins, (4) etherifying, in a second etherification zone, in the presence of at least one alcohol that has 1 to 4 carbon atoms per molecule and an etherification catalyst, a portion of the etherifiable olefins that are included in said isomerization effluent of (3) to obtain an etherified effluent.

2. A process according to claim 1, wherein the hydrocarbon effluent of (2') for use in the isomerization zone of (3) is substantially free of ethers.

3. A process according to claim 2, wherein the hydrocarbon effluent of (2') for use in the isomerization zone of (3) is substantially free of alcohol(s).

4. A process according to claim 1, wherein the isomerization is a hydroisomerization.

5. A process according to claim 4, wherein (2) and (3) are carried out in a single reaction zone.

6. A process according to claim 4, wherein (3) and (4) are carried out in a single reaction zone.

7. A process according to claim 1, wherein the isomerization is a skeletal isomerization.

8. A process according to claim 1, wherein the separation of (2) is a distillation process.

9. A process according to claim 1, further comprising (5) washing with water a portion of the etherified effluent of (4) in a washing zone that makes it possible to obtain a water and alcohol effluent and a hydrocarbon effluent.

10. A process according to claim 9, further comprising (6) distilling a portion of the hydrocarbon effluent of (5) into an ether effluent and a hydrocarbon effluent.

11. A process according to claim 1, further comprising (5) distilling a portion of the etherified effluent of (4) in a distillation zone into an ether effluent that comprises at least 70% ethers by weight and into a hydrocarbon and alcohol effluent.

12. A process according to claim 11, further comprising (6) washing a portion of the hydrocarbon and alcohol effluent of (5) in a washing zone that makes it possible to obtain an alcohol and water effluent and a hydrocarbon effluent.

13. A process according to claim 11, wherein a portion of the ether effluent of (2) is added to the etherified effluent of (4) for distillation in (5).

14. A process according to claim 1 further comprising (3') distilling, in an additional distillation zone, the isomerization effluent of (3), to obtain a light hydrocarbon effluent, comprising less than six (six excluded) carbon atoms per molecule, and a purified isomerization effluent that is used in stage (4).

15. A process according to claim 1, wherein the ether effluent of (2) comprises greater than 70% by weight ethers.

* * * * *